United States Patent [19]

Crounse et al.

[11] 4,028,372

[45] June 7, 1977

[54] METAL CHELATES OF 1-IMINO-3-(4-THIOXO-5-THIAZOLIDINYLIDENE)ISOINDOLINES

[75] Inventors: Nathan N. Crounse; Nicholas A. Ambrosiano, both of Cincinnati, Ohio

[73] Assignee: Sterling Drug Inc., New York, N.Y.

[22] Filed: Nov. 19, 1975

[21] Appl. No.: 633,246

Related U.S. Application Data

[63] Continuation-in-part of Ser. No. 496,078, Aug. 9, 1974, Pat. No. 3,966,753.

[30] Foreign Application Priority Data

July 28, 1975 United Kingdom ............ 31506/75

[52] U.S. Cl. .............................................. 260/299
[51] Int. Cl.$^2$ ................. C07F 15/00; C07F 15/04; C09B 57/00

[58] Field of Search .................................. 260/299

[56] References Cited

FOREIGN PATENTS OR APPLICATIONS 2,357,830  6/1974  Germany

*Primary Examiner*—Donald G. Daus
*Assistant Examiner*—D. G. Rivers
*Attorney, Agent, or Firm*—Lynn T. Fletcher; B. Woodrow Wyatt

[57] ABSTRACT

This invention relates to novel compounds of the isoindoline series. More particularly, the present invention relates to certain novel 1-imino-3-(2-oxo-4-thioxo-5-thiazolidinylidene)isoindolines, 1-imino-3-(2,4-dithioxo-5-thiazolidinylidene)isoindolines, water-insoluble pigments prepared therefrom, and to methods for their preparation.

9 Claims, No Drawings

METAL CHELATES OF 1-IMINO-3-(4-THIOXO-5-THIAZOLIDINYLIDENE)ISOINDOLINES

This application is a continuation-in-part of our prior copending application Ser. No. 496,078, filed on Aug. 9, 1974, now U.S. Pat. No. 3,966,753.

BACKGROUND OF THE INVENTION a. Field of the Invention

The invention described herein relates to new and useful compounds classified in the art of chemistry as 1-imino-3-(4-thioxo-5-thiazolidinylidene)isoindolines, to valuable metal chelate pigments derived therefrom and to intermediates and processes for obtaining them.

b. Description of the Prior Art

Metallized organic pigments of widely diverse stuctural types are known in the prior art. Among the more important classes of such metallized pigments may be mentioned, for example, metal chelates of: ortho-hydroxy azo pigments as described in U.S. Pat. No. 1,232,551; azomethine metal complex pigments as taught in U.S. Pat. No. 3,687,991; metallized porphyrin pigments as described in Berichte 60: 2611 (1927) [Chemical Abstracts 22: 1163 (1928)]; and metallized porphyrazine pigments as described in U.S. Pat. No. 2,765,308. The closest related prior art appears to lie in the class of pigments known as metallized tetrabenzoporphyrazines or metallized phthalocyanines. These compounds are well known and have been extensively described in Chapter 9 of The American Chemical Society monograph entitled "The Chemistry of Synthetic Dyes and Pigments", edited by H. A. Lubs, Reinhold Publishing Corporation, 430 Park Ave., New York, N.Y. (1955), as well as in many U.S. patents, particularly those in the Patent Office classification 260-314.5 entitled "Phthalocyanines".

There are a number of U.S. patents in the prior art which teach the use of 1,3-diimino-isoindolines as intermediates in the preparation of dyes and pigments. For example, U.S. Pat. No. 3,646,033 teaches the production of asymmetrically disubstituted isoindoline dyestuffs. Specifically disclosed therein is the interaction of 1,3-diimino-isoindoline and 1-phenyl-3-methyl-5-pyrazolone to form 1-[(1'-phenyl-3'-methyl-5'-oxo)-pyrazolidene-4']-3-iminoisoindoline which, in turn, is further interacted to introduce a second substituent in the 3-position forming a compound useful as a dyestuff.

SUMMARY OF THE INVENTION

In one of its composition of matter aspects, the invention relates to the novel metal chelate pigments of the formula

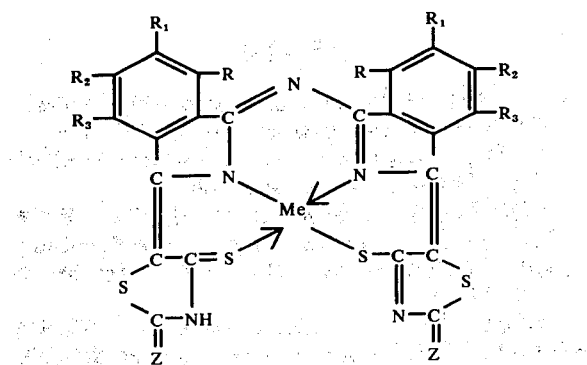

Formula I which are useful for coloring natural fibers, synthetic fiberforming materials such as threads, sheets, fibers, filaments, textile fabrics, paper, varnishes, inks, coatings and plastics.

In a second composition of matter aspect, the invention relates to certain novel 1-iminio-3-(4-thioxo-5-thiazolidinylidene)isoindolines represented by the formula

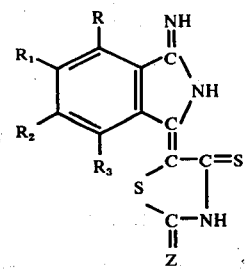

Formula II

In one of its process aspects, the invention relates to a process for preparing the metal chelate pigment final products of Formula I which comprises interacting approximately two molecular equivalents of a 1-iminio-3-(4-thioxo-5-thiazolidinylidene)isoindolines of Formula II with approximately one molecular equivalent of a salt of a divalent metal, Me.

In the second of its process aspects, the invention relates to a process for preparing the novel 1-imino-3-(4-thioxo-5-thiazolidinylidene)isoindolines of Formula II which comprises interacting a 1,3-diiminoisoindoline and a 4-thioxothiazolidine.

DETAILED DESCRIPTION INCLUSIVE OF THE PREFERRED EMBODIMENTS

More specifically, this invention, in its first composition of matter aspect, resides in the novel metal chelate pigments of the formula

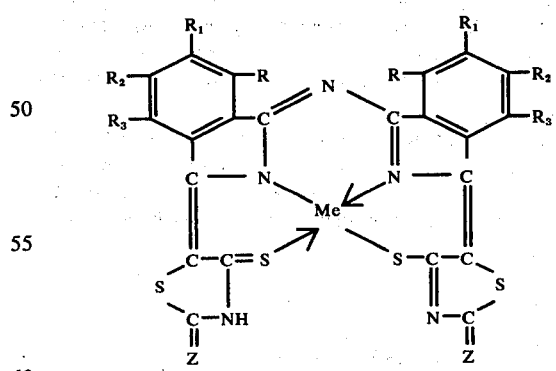

Formula I in which R, $R_1$, $R_2$ and $R_3$ are the same or different and are selected from the class consisting of hydrogen, alkyl having 1 to 3 carbon atoms, alkoxy having 1 to 3 carbon atoms, halo, trifluoromethyl, phenyl and phenyl substituted by alkyl having 1 to 3 carbon atoms, alkoxy having 1 to 3 carbon atoms or halogen; Me is a metal selected from the class consisting of copper, cobalt and nickel; and Z is oxygen or sulfur.

A particularly preferred embodiment of the abovedescribed composition of matter aspect are the nickel compounds of the formula

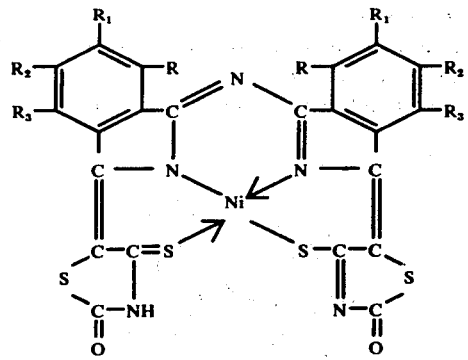

Formula III in which R, $R_1$, $R_2$ and $R_3$ each have the same respective meanings indicated in relation to Formula I.

The invention sought to be patented, in a second composition of matter aspect, resides in the novel 1-imino-3-(4-thioxo-5-thiazolidinylidene)isoindolines represented by the formula

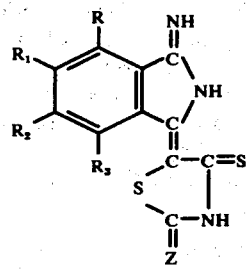

Formula II wherein R, $R_1$, $R_2$ and $R_3$ are the same or different and are selected from the class consisting of hydrogen, alkyl having 1 to 3 carbon atoms, alkoxy having 1 to 3 carbon atoms, halo, trifluoromethyl, phenyl and phenyl substituted by alkyl having one to three carbon atoms, alkoxy having one to three carbon atoms or halogen; and Z is O or S.

Particularly preferred embodiments in accordance with the second composition of matter aspect are the novel 1-imino-3-(2-oxo-4-thioxo-5-thiazolidinylidene)isoindolines of Formula II wherein Z is oxygen of the formula

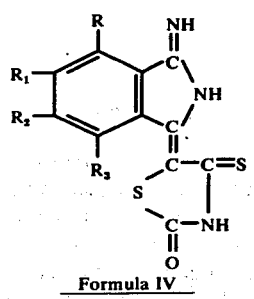

Formula IV in which R, $R_1$, $R_2$ and $R_3$ each have the same respective meanings indicated in relation to Formula II.

It will, of course, be understood by those skilled in the art that the compounds of this invention, both final products and intermediates, may exist and may be represented in any one of several tautomeric forms. However, structural determinations lead to the conclusion that the forms depicted by the structural formulas and as named are the most likely under ordinary conditions.

In the first of its process aspects, the invention sought to be patented resides in the process which comprises interacting approximately two molecular equivalents of a compound of the formula

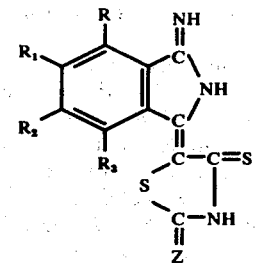

Formula II with approximately one molecular equivalent of a salt, of a divalent metal, Me, wherein Me, R, $R_1$, $R_2$, $R_3$ and Z each have the same respective meanings given in relation to Formula I and Formula II above.

In a second process aspect, the invention sought to be patented resides in the process for preparing the novel 1-imino-3-(4-thioxo-5-thiazolidinylidene)isoindolines of Formula II which comprises interacting in approximately equimolecular proportions a compound of the formula

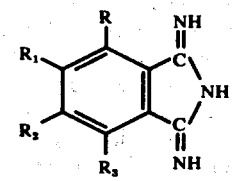

Formula V and a compound of the formula

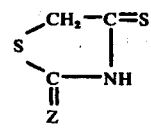

Formula VI wherein R, $R_1$, $R_2$, $R_3$ and Z each have the same respective meanings given in relation to Formula II above.

As used throughout, the term "halogen" includes bromine, chlorine, fluorine and iodine.

As used herein, the term "alkyl having 1 to 3 carbon atoms" includes saturated straight- or branched-chain aliphatic radicals represented by methyl, ethyl, propyl and isopropyl.

Similarly, the term "alkoxy having 1 to 3 carbon atoms" includes straight- or branched-chain aliphatic groups attached to the oxygen atom. Included in this term are methoxy, ethoxy, propoxy and isopropoxy.

The compounds of Formula I and Formula III, which are metal chelates of 1-imino-3-(4-thioxo-5-thiazolidinylidene)isoindolines are water-insoluble pigments, generally brown to green in shade.

They are useful for coloring natural fibers, synthetic fiber-forming material and cellulosic materials such as threads, sheets, fibers, filaments, textile fabrics and the like, as well as in the manufacture of paper, varnishes, inks, coatings and plastics. Because the pigments of this invention have good to excellent light-fastness, they are particularly suitable for the preparation of coatings that are designed for outdoor exposure such as automotive finishes.

The metal chelate pigments of this invention are useful for coloring or printing paper and cardboard as well as for coloring paper pulps. They are also useful for coloring and printing textile materials made from natural fibers, such as wool, cotton or linen, those made from semi-synthetic fibers, such as regenerated cellulose as represented by rayon or viscose or those made from synthetic fibers, such as polyaddition, polycondensation or polymerization compounds. Such colorings or printings can be carried out with the subject pigments in accordance with the usual pigment coloring and printing processes.

The metal chelate pigments of this invention are also useful for incorporation into lacquers and films of various constitution, for example, those made frrom cellulose acetate, cellulose propionate, polyvinyl chloride, polyethylene, polypropylene, polyamides, polyesters or alkyd resins. In addition, the subject compounds are suitable for coloring natural or synthetic resins, for example, acrylic resins, epoxy resins, polyester resins, vinyl resins, polystyrene resins or alkyd resins. When dispersed in a clear coating composition vehicle with the incorporation of a small amount of flake aluminum and the composition coated and cured on steel test panels, the subject pigments show excellent transparency, cleanliness and good intensity.

The metal chelate pigments of this invention are characterized by excellent light-fastness both under accelerated exposure evaluations and under prolonged outdoor exposure. Thus, when the subject pigments suspended in cured acrylic resin dispersion coated on foil-covered paper are exposed to carbon arc radiation, there is not loss in color value of the pigments after 300 hours of continuous exposure. Moreover, when steel test plates coated with a cured acrylic resin dispersion of the subject pigments were exposed for 12 months in Florida and Arizona, there was substantially no loss in color value or any indication of darkening.

The best mode contemplated by the inventors of carrying out this invention will now be described so as to enable any person skilled in the art to which it pertains to make and use the same.

Generally speaking, the novel metal chelate pigments of Formula I are conveniently obtained in accordance with the first process aspect of this invention by interacting approximately two molecular equivalents of the appropriate 1-imino-3-(4-thioxo-5-thiazolidinylidene)isoindoline of Formula II with one molecular equivalent of a salt of copper (II), cobalt (II) or nickel (II) which is soluble in aprotic or protic solvents. The choice of the anion is not critical in the operation of the preparative processes. Accordingly, by way of illustration and without limitation thereto, the anion can be, for example, bromide, chloride, iodide, nitrate, acetate, p-toluenesulfonate and the like. The reaction is preferably carried out at a temperature between about 0° C and 100° C in either an aprotic or protic solvent. Aprotic solvents suitable for the reaction are, for example, dimethylformamide, dimethylsulfoxide and hexamethylphosphoramide. Among protic solvents useful for this reaction are, for example, water; lower-aliphatic alcohols, for instance, methanol, ethyl alcohol, isopropyl alcohol, etc.; and ether glycols, for instance, 2-methoxyethanol, 2-ethoxyethanol, etc.

The novel 1-imino-3-(4-thioxo-5-thiazolidinylidene)isoindolines represented by Formula II, which are used to prepare the metal chelate pigments of Formula I are readily prepared in accordance with a second process aspect of this invention by the condensation of the appropriate 1,3-diiminoisoindoline (Formula V) through one of the imino moieties with the loss of ammonia at the site of the active methylene moiety of the appropriate 4-thioxothiazolidine (Formula VI). The reaction proceeds smoothly at reflux in a lower-aliphatic alcohol such as methanol and is preferably carried out under an atmosphere of nitrogen.

The 4-thioxothiazolidines represented by Formula VI, which are required for the above reaction, are generally known in the art and are conveniently prepared by employing known chemical procedures. For example, the known 2-oxo-4-thioxothiazolidine (Formula VI where Z is O) is obtained by the treatment of 2,4-dioxothiazolidine with phosphorus pentasulfide. The starting material 2,4-dithioxothiazolidine (Formula Vi where Z is S) is prepared by interacting commercially available 4-oxo-2-thioxothiazolidine with phosphorus pentasulfide.

The 1,3-diiminoisoindolines of Formula V are a known class of compounds readily obtained by procedures well-known in the prior art. For example, an appropriate phthalonitrile is interacted with ammonia or with a substance which gives off ammonia under the reaction conditions, for instance urea, to produce the corresponding 1,3-diiminoisoindoline. For example, the following 1,3-diiminoisoindolines of Formula V are useful starting materials for preparing the 1-imino-3-(4-thioxo-5-thiazolidinylidene)isoindolines represented by Formula II above.

1,3-Diiminoisoindoline
5-Methyl-1,3-diiminoisoindoline
4,5-Dimethyl-1,3-diiminoisoindoline
4,5,6,7-Tetraethyl-1,3-diiminoisoindoline
4,5,7-Trimethyl-1,3-diiminoisoindoline
4-Isopropyl-7-methyl-1,3-diiminoisoindoline
4,7-Dimethoxy-1,3-diiminoisoindoline
4,5-Dipropyl-7-ethoxy-1,3-diiminoisoindoline
5-Ethoxy-1,3-diiminoisoindoline
4,5,7-Trimethoxy-1,3-diiminoisoindoline
4,7-Diethoxy-1,3-diiminoisoindoline
4-Chloro-1,3-diiminoisoindoline
5-Bromo-1,3-diiminoisoindoline
5,6-Dichloro-1,3-diiminoisoindoline
4,5,6,7-Tetrachloro-1,3-diiminoisoindoline
5,6-Dibromo-4,7-difluoro-1,3-diiminoisoindoline
5-Chloro-4,6,7-trifluoro-1,3-diiminoisoindoline
5,6-Diiodo-4,7-dimethoxy-1,3-diiminoisoindoline
4,7-Difluoro-1,3-diiminoisoindoline
4,5,6,7-Tetrabromo-1,3-diiminoisoindoline
4-Phenyl-1,3-diiminoisoindoline
4-Methyl-5,6,7-triphenyl-1,3-diiminoisoindoline
7-Ethoxy-4-methyl-5-phenyl-1,3-diiminoisoindoline 4,5,6,7-Tetraphenyl-1,3-diiminoisoindoline
5-(2,4,5-Trimethylphenyl)-1,3-diiminoisoindoline
4-(3,4-Dimethoxyphenyl)-1,3-diiminoisoindoline
4-(p-Chlorophenyl)-1,3-diiminoisoindoline
4-(p-Bromophenyl)-7-phenyl-1,3-diiminoisoindoline
4,5,7-Triphenyl-1,3-diiminoisoindoline The stuructures of the compounds of this invention were established by the modes of synthesis, by elementary analysis of representative samples, and by ultraviolet, infrared, nuclear magnetic resonance and mass spectral analyses. The course of the reactions for the preparation of the intermediates and their consumption in the chelating reactions was followed by the use of thin layer chromatography.

The invention is illustrated by the following examples, without, however, being limited thereto. Melting points are uncorrected unless otherwise indicated. In the following examples, the term "parts" is in each instance used to indicate parts by weight and the relationship of parts by weight to parts by volume is the same as that of the kilogram to the liter.

EXAMPLE 1

A. To a stirred solution of 49.7 parts of 2-oxo-4-thioxothiazolidine in 990 parts of methanol there was added at 40° C and under an atmosphere of nitrogen 54.3 parts of powdered 1,3-diiminoisoindoline. Initially, a thick slurry resulted. The reaction mixture was stirred at room temperature for 2 hours during which time the mixture gradually thinned. The mixture was then heated at reflux for approximately 2 hours and after cooling to 25° C, was filtered. The collected solid was washed with fresh methanol and dried in vacuo at 50° C to obtain 1-imino-3-(2-oxo-4-thioxo-5-thiazolidinylidene)isoindoline as an orange powder melting at 267°–8° C (dec.).

Anal. Calcd. for $C_{11}H_7N_3OS_2$: C 50.56; H 2.70; N 16.08; S 24.54. Found: C 50.36; H 2.53; N 16.25; S 24.38.

This compound, which corresponds to Formula IV wherein R, $R_1$, $R_2$ and $R_3$ are each hydrogen, was found on testing in vitro by standard serial dilution procedures to be bacteriostatic versus: *Staphylococcus aureus* Smith at a minimal concentration of 62.5 parts per million; *Esherichia coli* Vogel at 125 parts per million; *Klebsiella pneumoniae* 39645 at 125 parts per million; *Proteus mirabilis* MGH-1 at 125 parts per million; *Pseudomonas aeruginosa* MGH-2 at 125 parts per million. The compound was also found to be fungistatic versus: *Tricophyton mentagrophytes* 9129 at 62.5 parts per million; *Aspergillus niger* 16404 at 125 parts per million and *Candida albicans* 10231 at 125 parts per million.

B. To a stirred solution of 2.7 parts of nickel (II) p-toluenesulfonate hexahydrate in 100 parts of dimethylformamide there was added at room temperature 2.6 parts of finely powdered 1-imino-3-(2-oxo-4-thioxo-5-thiazolidinylidene)isoindoline. The mixture was stirred for one hour at ambient temperature and then during 3½ hours was heated to 100° C. Heating at 100° C was continued for 2 hours. The reaction mixture was cooled to room temperature, filtered and the collected solid was washed successively with small amounts of fresh dimethylformamide, water and acetone and then dried in vacuo at 50° C to obtain 2.2 parts of the dark-green nickel chelate pigment represented by Formula III wherein R, $R_1$, $R_2$ and $R_3$ are each hydrogen.

Anal. Calcd. for $C_{22}H_9N_5NiS_4O_2$: C 46.99; H 1.61; N 12.45; S 22.81; Ni 10.44. Found: C 46.88; H 1.50; N 12.62; S 22.72; Ni 10.39.

EXAMPLE 2

A. A solution of 7.2 parts of 1,3-diiminoisoindoline in 100 parts of methanol was added to a solution of 7.2 parts of 2,4-dithioxo-thiazolidine in 75 parts of methanol under an atmosphere of nitrogen. The mixture was stirred at room temperature for 24 hours and the solid which separated was collected by filtration, washed with a small volume of fresh methanol and dried in vacuo at 50° C to obtain 1-imino-3-(2,4-dithioxo-5-thiazolidinylidene)isoindoline as a red-orange crystalline solid which sintered at 268°–270° C.

Anal. Calcd. for $C_{11}H_7N_3S_3$: C 47.62; H 2.55; N 15.15; S 34.66. Found: C 47.60; H 2.58; N 14.91; S 34.64.

This compound, which corresponds to Formula II wherein R, $R_1$, $R_2$ and $R_3$ are each hydrogen, and Z is sulfur, was found on testing in vitro by standard serial dilution procedures to be bacteriostatic versus: *Staphylococcus aureus* Smith at a minimal concentration of 125 parts per million; *Esherichia C.Li* Vogel at greater than 125 parts per million; *Klebsiella pneumoniae* 39645 at 125 parts per million; *Proteus mirabilis* MGH-1 at greater than 125 parts per million; *Pseudomonas aeruginosa* MGH-2 at greater than 125 parts per million. The compound was also found to be fungistatic versus: *Tricophyton mentagrophytes* 9129 at greater than 250 parts per million; *Aspergillus niger* 16404 at greater than 125 parts per million and *Candida albicans* 10231 at greater than 125 parts per million.

B. To a stirred solution of 2.7 parts of nickel (II) p-toluenesulfonate hexahydrate in 100 parts of dimethylformamide there was added at room temperature 2.7 parts of finely powdered 1-imino-3-(2,4-dithioxo-5-thiazolidinylidene)isoindoline. The reaction mixture was stirred at ambient temperature for 18 hours and then filtered. The collected solid was washed successively with fresh dimethylformamide, water and acetone and then dried in vacuo at 50° C to obtain 1.9 parts of crude product. The product was then extracted several times with small amounts of dimethylformamide at 100° C and again dried to obtain the red-brown pigment represented by Formula I wherein Z is sulfur; Me is nickel; and R, $R_1$, $R_2$ and $R_3$ are each hydrogen.

EXAMPLE 3

A. Proceeding in a manner similar to that described above in Example 1, part A, but substituting an equivalent amount of 5-methyl-1,3-diiminoisoindoline for the 1,3-diiminoisoindoline used in that example, there is obtained 1-imino-5-methyl-3-(2-oxo-4-thioxo-5-thiazolidinylidene)isoindoline.

B. When an equivalent amount of 1-imino-5-methyl-3-(2-oxo-4-thioxo-5-thiazolidinylidene)isoindoline is substituted for the 1-imino-3-(2-oxo-4-thioxo-5-thiazolidinylidene)isoindoline in the procedure described in Example 1, part B above, there is obtained as the product a nickel chelate pigment corresponding to Formula III in which R, $R_1$ and $R_3$ are each hydrogen, and $R_2$ is methyl.

EXAMPLE 4

A. Using a procedure similar to that described in Example 2, part A above, but substituting 4,5-dimethyl-1,3-diiminoisoindoline for the 1,3-diiminoisoindoline used in that example, there is obtained as the product 1-imino-4,5-dimethyl-3-(2,4-dithioxo-5-thiazolidinylidene)isoindoline.

B. Following the procedure described in Example 2, part B above, but using an equivalent amount of 1-imino-4,5-dimethyl-3-(2,4-dithioxo-5-thiazolidinylidene)isoindoline in place of 1-imino-3-(2,4-dithioxo-5-thiazolidinylidene)isoindoline, there is obtained as the product a nickel chelate pigment corresponding to Formula I in which Z is S; Me is nickel; $R_2$ and $R_3$ are each methyl; and R and $R_1$ are each hydrogen.

EXAMPLE 5

A. When an equivalent amount of 4,5,6,7-tetraethyl-1,3-diiminoisoindoline is substituted for the 1,3-diiminoisoindoline in the procedure described in Example 1, part A above, there is obtained as the product 1-imino-4,5,6,7-tetraethyl-3-(2-oxo-4-thioxo-5-thiazolidinylidene)isoindoline.

B. By substituting an equivalent amount of 1-imino-4,5,6,7-tetraethyl-3-(2-oxo-4-thioxo-5-thiazolidinylidene)isoindoline for the 1-imino-3-(2-oxo-4-thioxo-5-thiazolidinylidene)isoindoline in the procedure described in Example 1B above, there is obtained the nickel chelate pigment represented by Formula III above wherein R, $R_1$, $R_2$ and $R_3$ are each ethyl.

EXAMPLE 6

A. Following the procedure described in Example 2, part A above, but using equivalent amounts of 4,5,7-trimethyl-1,3-diiminoisoindoline in place of 1,3-diiminoisoindoline, there is obtained as the product, 1-imino-4,5,7-trimethyl-3-(2,4-dithioxo-5-thiazolidinylidene)isoindoline.

B. When an equivalent amount of 1-imino-4,5,7-trimethyl-3-(2,4-dithioxo-5-thiazolidinylidene)isoindoline is substituted for 1-imino-3-(2,4-dithioxo-5-thiazolidinylidene)isoindoline in the procedure described in Example 2, part B above, there is obtained as the product a nickel chelate pigment corresponding to Formula I in which Z is S; Me is nickel; R, $R_2$ and $R_3$ are each methyl; and $R_1$ is hydrogen.

EXAMPLE 7

A. Proceeding in a manner similar to that described above, in Example 2, part A, but substituting an equivalent amount of 4-isopropyl-7-methyl-1,3-diiminoisoindoline for the 1,3-diiminoisoindoline used in that example, there is obtained 1-imino-4-isopropyl-7-methyl-3-(2,4,-dithioxo-5-thiazolidinylidene)isoindoline.

B. When an equivalent amount of 1-imino-4-isopropyl-7-methyl-3-(2,4-dithioxo-5-thiazolidinylidene)isoindoline is substituted for the 1-imino-3-(2,4,-dithioxo-5-thiazolidinylidene) isoindoline in the procedure described in Example 2, part B above, there are each obtained as the product a nickel chelate pigment corresponding to Formula I in which Z is S; Me is nickel; R is methyl; $R_3$ is isopropyl; and $R_1$ and $R_2$ are hydrogen.

EXAMPLE 8

A. Using a procedure similar to that described in Example 2, part A above, but substituting 4,7-dimethoxy-1,3-diiminoisoindoline, there is obtained as the product 1-imino-4,7-dimethoxy-3-(2,4-dithioxo-5-thiazolidinylidene)isoindoline.

B. Following the procedure described in Example 2, part B above, but using an equivalent amount of 1-imino-4,7-dimethoxy-3-(2,4-dithioxo-5-thiazolidinylidene)isoindoline in place of 1-imino-3-(2,4-dithioxo-5-thiazolidinylidene)isoindoline, there is obtained as the product a nickel chelate pigment corresponding to Formula I in which Z is S; Me is nickel; R and $R_3$ are each methoxy; and $R_1$ and $R_2$ are each hydrogen.

EXAMPLE 9

A. When an equivalent amount of 4,5-dipropyl-7-ethoxy-1,3-diiminoisoindoline is substituted for 1,3-diiminoisoindoline in the procedure described in Example 1, part A above, there is obtained as the product 1-imino-4,5-dipropyl-7-ethoxy-3-(2-oxo-4-thioxo-5-thiazolidinylidene)isoindoline.

B. By substituting an equivalent amount of 1-imino-4,5-dipropyl-7-ethoxy-3-(2-oxo-4-thioxo-5-thiazolidinylidene)isoindoline for 1-imino-3-(2-oxo-4-thioxo-5-thiazolidinylidene) isoindoline in the procedure described in Example 1B above, there is obtained the nickel chelate pigment represented by Formula III above where R is ethoxy; $R_1$ is hydrogen, and $R_2$ and $R_3$ are each propyl.

EXAMPLE 10

A. Following the procedure described in Example 2, part A above, but using an equivalent amount of 5-ethoxy-1,3-diiminoisoindoline in place of 1,3-diiminoisoindoline, there is obtained as the product 1-imino-5-ethoxy-3-(2,4-dithioxo-5-thiazolidinylidene)isoindoline.

B. When an equivalent amount of 1-imino-5-ethoxy-3-(2,4-dithioxo-5-thiazolidinylidene)isoindoline is substituted for 1-imino-3-(2,4-dithioxo-5-thiazolidinylidene)isoindoline in the procedure described in Example 2, part B above, there is obtained as the product a nickel chelate pigment corresponding to Formula I in which Z is S; Me is nickel; $R_2$ is ethoxy; and R, $R_1$ and $R_3$ are each hydrogen.

EXAMPLE 11

To a stirred solution of 1.9 parts of copper (II) chloride dihydrate in 125 parts of dimethylformamide, there was added at 25° C 5.2 parts of finely powdered 1-imino-3-(2-oxo-4-thioxo-5-thiazolidinylidene)isoindoline which was prepared according to the procedure described in Example 1A hereinabove. The mixture was stirred for 1 hour at ambient temperature and then heated to 100° C during a period of 30 minutes. Heating at 100° C was maintained for two hours. The reaction mixture was then cooled to room temperature and filtered. The solid collected by filtration was washed with fresh dimethylformamide, then with water and was dried in vacuo at 50° C to obtain the dark green pigment represented by Formula I wherein Me is copper; Z is O; and R, $R_1$, $R_2$ and $R_3$ are each hydrogen.

EXAMPLE 12

To a stirred solution of 2.6 parts of cobalt (II) chloride hexahydrate in 125 parts of dimethylformamide, there was added at 25° C 5.2 parts of finely powdered 1-imino-3(2-oxo-4-thioxo-5-thiazolidinylidene)isoindoline which was prepared according to the procedure described in Example 1A hereinbefore. The resultant dark brown solution was stirred at ambient temperature for one hour and was then rapidly heated to 100°

C. Heating at 100° C was maintained for a period of 2 hours during which period a dark precipitate gradually formed. The reaction mixture was cooled to 25° C and filtered. The solid collected by the filtration was washed first with fresh dimethylformamide and then with water and was dried in vacuo at 50° C to obtain a dark brown pigment represented by Formula I wherein Me is cobalt; Z is O; and R, $R_1$, $R_2$ and $R_3$ are each hydrogen.

EXAMPLE 13

A. Proceeding in a manner similar to that described above in Example 1, part A, but substituting an equivalent amount of 4,5,7-trimethoxy-1,3-diiminoisoindoline for the 1,3-diiminoisoindoline used in that example, there is obtained 1-imino-4,5,7-trimethoxy-3-(2-oxo-4-thioxo-5-thiazolidinylidene)isoindoline.

B. When an equivalent amount of 1-imino-4,5,7-trimethoxy-3-(2-oxo-4-thioxo-5-thiazolidinylidene)isoindoline is substituted for 1-imino-3-(2-oxo-4-thioxo-5-thiazolidinylidene) isoindoline in the procedure described in Example 11 above, there is obtained as the product a copper chelate pigment corresponding to Formula I in which Z is O; Me is copper; $R_1$ is hydrogen; and R, $R_2$ and $R_3$ are each methoxy.

EXAMPLE 14

A. Using a procedure similar to that described in Example 2, part A above, but substituting 4,7-diethoxy-1,3-diiminoisoindoline for 1,3-diiminoisoindoline, there is obtained as the product 1-imino-4,7-diethoxy-3-(2,4-dithioxo-5-thiazolidinylidene)isoindoline.

B. Following the procedure described in Example 12 above, but using an equivalent amount of 1-imino-4,7-diethoxy-3-(2,4-dithioxo-5-thiazolidinylidene)isoindoline in place of 1-imino-3-(2-oxo-4-thioxo-5-thiazolidinylidene)isoindoline, there is obtained as the product a cobalt chelate pigment corresponding to Formula I in which Z is S; Me is cobalt; R and $R_3$ are each ethoxy; and $R_1$ and $R_2$ are each hydrogen.

EXAMPLE 15

A. Proceeding in a manner similar to that described above in Example 1, part A, but substituting an equivalent amount of 4-chloro-1,3-diiminoisoindoline for the 1,3-diiminoisoindoline used in that example, there is obtained 1-imino-4-chloro-3-(2-oxo-4-thioxo-4-thizaolidinylidene)isoindoline.

B. When an equivalent amount of 1-imino-4-chloro-3-(2-oxo-4-thioxo-5-thiazolidinylidene)isoindoline is substituted for 1-imino-3-(2-oxo-4-thioxo-5-thiazolidinylidene)isoindoline in the procedure described in Example 1, part B above, there is obtained as the product a nickel chelate pigment corresponding to Formula III in which R, $R_1$ and $R_2$ are each hydrogen; and $R_3$ is Cl.

EXAMPLE 16

A. When an equivalent amount of 5-bromo-1,3-diiminoisoindoline indoline is substituted for 1,3-diiminoisoindoline in the procedure described in Example 2, part A above, there is obtained as the product 1-imino-5-bromo-3-(2,4-dithioxo-5-thiazolidinylidene)isoindoline.

B. By substituting an equivalent amount of 1-imino-5-bromo-3-(2,4-dithioxo-5-thiazolidinylidene)isoindoline for 1-imino-3-(2,4-dithioxo-5-thiazolidinylidene)isoindoline in the procedure described in Example 2B above, there is obtained the nickel chelate pigment represented by Formula I above where Z is S; Me is nickel; $R_2$ is Br; and R, $R_1$ and $R_3$ are each hydrogen.

EXAMPLE 17

A. Following the procedure described in Example 1, part A above, but using an equivalent amount of 5,6-dichloro-1,3-diiminoisoindoline in place of 1,3-diiminoisoindoline, there is obtained as the product 1-imino-5,6-dichloro-3-(2-oxo-4-thioxo-5-thiazolidinylidene)isoindoline.

B. When an equivalent amount of 1-imino-5,6-dichloro-3-(2-oxo-4-thioxo-5-thiazolidinylidene)isoindoline is substituted for 1-imino-3-(2-oxo-4-thioxo-5-thiazolidinylidene)isoindoline in the procedure described in Example 11 above, there is obtained as the product a copper chelate pigment corresponding to Formula I in which Z is O; Me is copper; $R_1$ and $R_2$ are each Cl; and R and $R_3$ are each hydrogen.

EXAMPLE 18

A. Proceeding in a manner similar to that described above in Example 2, part A, but substituting an equivalent amount of 4,5,6,7-tetrachloro-1,3-diiminoisoindoline for 1,3-diiminoisoindoline used in that example, there is obtained 1-imino-4,5,6,7-tetrachloro-3-(2,4-dithioxo-5-thiazolidinylidene)isoindoline.

B. When an equivalent amount of 1-imino-4,5,6,7-tetrachloro-3-(2,4-dithioxo-5-thiazolidinylidene)isoindoline is substituted for 1-imino-3-(2,4-dithioxo-5-thiazolidinylidene)isoindoline in the procedure described in Example 2, part B above, there is obtained as the product a nickel chelate pigment corresponding to Formula I in which Z is S; Me is nickel; and R, $R_1$, $R_2$ and $R_3$ are each Cl.

EXAMPLE 19

A. Using a procedure similar to that described in Example 1, part A above, but substituting 5,6-dibromo-4,7-difluoro-1,3-diiminoisoindoline for 1,3-diiminoisoindoline, there is obtained as the product 1-imino-5,6-dibromo-4,7-difluoro-3-(2-oxo-4-thioxo-5-thiazolidinylidene)isoindoline.

B. Following the procedure described in Example 12 above, but using an equivalent amount of 1-imino-5,6-dibromo-4,7-difluoro-3-(2-oxo-4-thioxo-5-thiazolidinylidene)isoindoline in place of 1-imino-3-(2-oxo-4-thioxo-5-thiazolidinylidene)isoindoline there is obtained as the product a cobalt chelate pigment corresponding to Formula I in which Z is O; Me is cobalt; $R_1$ and $R_2$ are each Br; and R and $R_3$ are each F.

EXAMPLE 20

A. When an equivalent amount of 5-chloro-4,6,7-trifluoro-1,3-diiminoisoindoline is substituted for 1,3-diiminoisoindoline in the procedure described in Example 1, part A above, there is obtained as the product 1-imino-5-chloro-4,6,7-trifluoro-3-(2-oxo-4-thioxo-5-thiazolidinylidene)isoindoline.

B. By substituting an equivalent amount of 1-imino-5-chloro-4,6,7-trifluoro-3-(2-oxo-4-thioxo-5-thiazolidinylidene) isoindoline for 1-imino-3-(2-oxo-4-thioxo-5-thiazolidinylidene isoindoline in the procedure described in Example 1B above, there is obtained the nickel chelate pigment represented by Formula III above, wherein $R_2$ is Cl; and R, $R_1$ and $R_3$ are each F.

EXAMPLE 21

A. Following the procedure described in Example 2, part A above, but using equivalent amounts of 5,6-diiodo-4,7-dimethoxy-1,3-diiminoisoindoline in place of 1,3-diiminoisoindoline, there is obtained as the product 1-imino-5,6-diiodo-4,7-dimethoxy-3-(2,4-dithoxo-5-thiazolidinylidene)isoindoline.

B. When an equivalent amount of 1-imino-5,6-diiodo-4,7-dimethoxy-3-(2,4-dithoxo-5-thiazolidinylidene)isoindoline is substituted for 1-imino-3-(2,4-dithoxo-5-thiazolidinylidene) isoindoline in the procedure described in Example 2, part B above, there is obtained as the product a nickel chelate pigment corresponding to Formula I wherein Z is S; Me is nickel; $R_1$ and $R_2$ are each I; and R and $R_3$ are each methoxy.

EXAMPLE 22

A. Proceeding in a manner similar to that described above in Example 2, part A, but substituting an equivalent amount of 4,7-difluoro-1,3-diiminoisoindoline for 1,3-diiminoisoindoline used in that example, there is obtained 1-imino-4,7-difluoro-3-(2,4-dithoxo-5-thiazolidinylidene)isoindoline.

B. When an equivalent amount of 1-imino-4,7-difluoro-3-(2,4-dithoxo-5-thiazolidinylidene)isoindoline is substituted for 1-imino-3-(2-oxo-4-thioxo-5-thiazolidinylidene)isoindoline in the procedure described in Example 12 above, there is obtained as the product a cobalt chelate pigment corresponding to Formula I in which Z is S; Me is cobalt; $R_1$ and $R_2$ are each hydrogen; and R and $R_3$ are each F.

EXAMPLE 23

A. Using a procedure similar to that described in Example 1, part A above, but substituting 4,5,6,7-tetrabromo-1,3-diiminoisoindoline for 1,3-diiminoisoindoline, there is obtained as the product 1-imino-4,5,6,7-tetrabromo-3-(2-oxo-4-thioxo-5-thiazolidinylidene)isoindoline.

B. Following the procedure described in Example 1, part B above, but using an equivalent amount of 1-imino-4,5,6,7-tetrabromo-3-(2-oxo-4-thioxo-5-thiazolidinylidene)isoindoline in place of 1-imino-3-(2-oxo-4-thioxo-5-thiazolidinylidene) isoindoline, there is obtained as the product a nickel chelate pigment corresponding to Formula III in which R, $R_1$, $R_2$ and $R_3$ are each Br.

EXAMPLE 24

A. When an equivalent amount of 4-phenyl-1,3-diiminoisoindoline is substituted for 1,3-diiminoisoindoline in the procedure described in Example 1, part A above, there is obtained as the product 1-imino-4-phenyl-3-(2-oxo-4-thioxo-5-thiazolidinylidene)isoindoline.

B. By substituting an equivalent amount of 1-imino-4-phenyl-3-(2-oxo-4-thioxo-5-thiazolidinylidene)isoindoline for 1-imino-3-(2-oxo-4-thioxo-5-thiazolidinylidene)isoindoline in the procedure described in Example 1B above, there is obtained the nickel chelate pigment represented by Formula III above wherein R, $R_1$ and $R_2$ are each hydrogen; and $R_3$ is phenyl.

EXAMPLE 25

A. Following the procedure described in Example 2, part A above, but using equivalent amounts of 4-methyl-5,6,7-triphenyl-1,3-diiminoisoindoline in place of 1,3-diiminoisoindoline, there is obtained as the product 1-imino-4-methyl-5,6,7-triphenyl-3-(2,4-dithoxo-5-thiazolidinylidene)isoindoline.

B. When an equivalent amount of 1-imino-4-methyl-5,6,7-triphenyl-3-(2,4-dithoxo-5-thiazolidinylidene)isoindoline is substituted for 1-imino-3-(2-oxo-4-thioxo-5-thiazolidinylidene) isoindoline in the procedure described in Example 11 above, there is obtained as the product a copper chelate pigment corresponding to Formula I in which Z is S; Me is copper; R, $R_1$ and $R_2$ are each phenyl; and $R_3$ is methyl.

EXAMPLE 26

A. Proceeding in a manner similar to that described above in Example 1, part A, but substituting an equivalent amount of 7-ethoxy-4-methyl-5-phenyl-1,3-diiminoisoindoline for 1,3-diiminoisoindoline used in that example, there is obtained 1-imino-7-ethoxy-4-methyl-5-phenyl-3-(2-oxo-4-thioxo-5-thiazolidinylidene)isoindoline.

B. When an equivalent amount of 1-imino-7-ethoxy-4-methyl-5-phenyl-3-(2-oxo-4-thioxo-5-thiazolidinylidene)isoindoline is substituted for 1-imino-3-(2-oxo-4-thioxo-5-thiazolidinylidene)isoindoline in the procedure described in Example 1, part B above, there is obtained as the product a nickel chelate pigment corresponding to Formula III in which R is ethoxy; $R_1$ is hydrogen, $R_2$ is phenyl; and $R_3$ is methyl.

EXAMPLE 27

A. Using a procudure similar to that described in Example 1, part A above, but substituting 4,5,6,7-tetraphenyl-1,3-diiminoisoindoline for 1,3-diiminoisoindoline, there is obtained as the product 1-imino-4,5,6,7-tetraphenyl-3-(2-oxo-4-thioxo-5-thiazolidinylidene)isoindoline.

B. Following the procedure described in Example 1, part B above, but using an equivalent amount of 1-imino-4,5,6,7-tetraphenyl-3-(2-oxo-4-thioxo-5-thiazolidinylidene)isoindoline in place of 1-imino-3-(2-oxo-4-thioxo-5-thiazolidinylidene)isoindoline, there is obtained as the product a nickel chelate pigment corresponding to Formula III in which R, $R_1$, $R_2$ and $R_3$ are each phenyl.

EXAMPLE 28

A. When an equivalent amount of 5-(2,4,5-trimethylphenyl)-1,3-diiminoisoindoline is substituted for 1,3-diiminoisoindoline in the procedure described in Example 1, part A above, there is obtained as the product 1-imino-5-(2,4,5-trimethylphenyl)-3-(2-oxo-4-thioxo-5-thiazolidinylidene)isoindoline.

B. By substituting an equivalent amount of 1-imino-5-(2,4,5-trimethylphenyl)-3-(2-oxo-4-thioxo-5-thiazolidinylidene)isoindoline for 1-imino-3-(2-oxo-4-thioxo-5-thiazolidinylidene)isoindoline in the procedure described in Example 12 above, there is obtained the cobalt chelate pigment represented by Formula I above wherein Z is O; Me is cobalt; R, $R_1$ and $R_3$ are each hydrogen; and $R_2$ is 2,4,5-trimethylphenyl.

EXAMPLE 29

A. Following the procedure described in Example 2, part A above, but using an equivalent amount of 4-(3,4-dimethoxyphenyl)-1,3-diiminoisoindoline in place of 1,3-diiminoisoindoline, there is obtained as the product 1-imino-4-(3,4-dimethoxyphenyl)-3-(2,4-dithioxo-5-thiazolidinylidene)isoindoline.

B. When an equivalent amount of 1-imino-4-(3,4-dimethoxyphenyl)-3-(2,4-dithioxo-5-thiazolidinylidene)isoindoline is substituted for 1-imino-3-(2,4-dithioxo-5-thiazolidinylidene)isoindoline in the procedure described in Example 2, part B above, there is obtained as the product a nickel chelate pigment corresponding to Formula I where Z is S; Me is nickel; R, $R_1$ and $R_2$ are each hydrogen; and $R_3$ is 3,4-dimethoxyphenyl.

EXAMPLE 30

A. Using a procedure similar to that described in Example 2, part A aove, but substituting 4-(p-chlorophenyl)-1,3-diiminoisoindoline for 1,3-diiminoisoindoline, there is obtained as the product 1-imino-4-(p-chlorophenyl)-3-(2,4-dithioxo-5-thiazolidinylidene)isoindoline.

B. Following the procedure described in Example 11 above, but using an equivalent amount of 1-imino-4-(p-chlorophenyl)-3-(2,4-dithioxo-5-thiazolidinylidene)isoindoline in place of 1-imino-3-(2-oxo-4-thioxo-5-thiazolidinylidene)isoindoline, there is obtained as the product a copper chelate pigment corresponding to Formula I in which Z is S; Me is copper; R, $R_1$ and $R_2$ are each hydrogen; and $R_3$ is p-chlorophenyl.

EXAMPLE 31

A. Proceeding in a manner similar to that described above in Example 1, part A, but substituting an equivalent amount of 4-(p-bromophenyl)-7-phenyl-1,3-diiminoisoindoline for 1,3-diiminoisoindoline used in that example, there is obtained 1-imino-4-(p-bromophenyl)-7-phenyl-3-(2-oxo-4-thioxo-5-thiazolidinylidene)isoindoline.

B. When an equivalent amount of 1-imino-4-(b-bromophenyl)-7-phenyl-3-(2-oxo-4-thioxo-5-thiazolidinylidene)isoindoline is substituted for 1-imino-3-(2-oxo-4-thioxo-5-thiazolidinylidene) isoindoline in the procedure described in Example 12 above, there is obtained as the product a cobalt chelate pigment corresponding to Formula I in which Z is O; Me is cobalt; R is phenyl; $R_1$ and $R_2$ are each hydrogen; and $R_3$ is p-bromophenyl.

EXAMPLE 32

A. Following the procedure described in Example 2, part A above, but using an equivalent amount of 4,5,7-triphenyl-1,3-diiminoisoindoline in place of 1,3-diiminoisoindoline, there is obtained as the product 1-imino-4,5,7-triphenyl-3-(2,4-dithioxo-5-thiazolidinylidene)isoindoline.

B. When an equivalent amount of 1-imino-4,5,7-triphenyl-3-(2,4-dithioxo-5-thiazolidinylidene)isoindoline is substituted for 1-imino-3-(2,4-dithioxo-5-thiazolidinylidene)isoindoline in the procedure described in Example 2, part B above, there is obtained as the product a nickel chelate pigment corresponding to Formula I in which Z is S; Me is nickel, R, $R_2$ and $R_3$ are each phenyl; and $R_1$ is hydrogen.

EXAMPLE 33

This example is representative of one of the procedures employed for the evaluation of the novel pigments of this invention as coloring agents for coating compositions.

A mixture of two parts of the novel pigment obtained in Example 1, part B above, seven parts of an acrylic resin, four parts of xylol and 20 parts of one-sixteenth inch diameter steel balls was charged into a container which was placed in a mechanical shaker. Shaking was effected for 1 hour. The container was removed from the shaker and to the mixture there was added an additional 17 parts of the acrylic resin and an additional 10 parts of xylol. The container was again placed in the shaker and shaking was effected for fifteen minutes longer. The steel balls were removed from the mixture and portions of the composition, which contained approximately five percent pigment, were coated on foil-covered paper. The cured acrylic coating was completely transparent and was of a pleasing yellow-green shade. The coating was then tested for light-fastness under accelerated conditions by exposing the coated foil-covered specimens to radiation from a carbon arc in a standard light-fast testing apparatus. After 600 hours of continuous exposure, there was no observable loss in strength of shade.

EXAMPLE 34

The novel pigments of this invention were evaluated for use in preparing coating compositions suitable for outdoor exposure, such as automobile finishes. Representative of the method employed is the following description of the preparation and testing of a "metallic" automobile finish.

A pigment base was prepared by subjecting a mixture of 15.7 parts of the chelate pigment from Example 1, part B above, and 16.2 parts of acrylic resin dissolved in 24.6 parts of xylol to attrition in a steel ball mill (one-half inch balls) for 48 hours. To the milled mixture there was then added an additional 4.3 parts of acrylic resin dissolved in 26.2 parts of xylol. The pigment base, which contained 18 percent pigment was incorporated in a coating composition containing 7.7 parts of the pigment base, 3.3 parts of a 30 percent aluminum paste, 19.5 parts of acrylic resin, 15.2 parts of a melamine resin, 1.3 parts of butanol and 35 parts of xylol. The resultant composition was sprayed onto primed 4 × 12 inch steel test panels and the coated panels were then placed in a curing oven at 300° F for 30 minutes. There was thus produced a pleasing dark yellow-green transparent and glossy "metallic" finish on the test panels.

The coated panels were then tested by outdoor exposure in Florida and under desert sun in Arizona. After 12 months of continuous exposure, there was essentially no perceptible change in the hue, brightness and strength of the pigment.

EXAMPLE 35

A. To a mixture of 14.1 parts of 4,5,6,7-tetrachloro-1,3-diiminoisoindoline, 6.7 parts of 2-oxo-4-thioxo-thiazolidine and 10.0 parts of freshly prepared, ground anhydrous sodium acetate, there was added 157 parts of glacial acetic acid. The resulting slurry was heated at reflux under a continuous flow of nitrogen for approximately one hour. The reaction solution was cooled to room temperatrue, sealed under an atmosphere of nitrogen and set aside for about 60 hours. The solid which separated on standing was collected by filtration at room temperature, washed five times, each with 21.0 parts glacial acetic 28 and then a total of eight times, each with 20.0 parts distilled water. The water-wet pulp was stirred with 90.0 parts of 28 percent aqueous ammonia, filtered to remove any insolubles and the product reprecipitated by adjusting the pH of the solution to 6.0 by the addition of 99.2 parts of 6N hydrochloric acid solution. The solid was collected by filtration, washed with 3000 parts of water and air dried at 60° C. to obtain 1-imino-4,5,6,7-tetrachloro-3-(2-oxo-4-thioxo-5-thiazolidinylidene)isoindoline as a brown powder which did not melt up to 340° C.

B. To a stirred solution of 4.0 parts of 1-imino-4,5,6,7-tetrachloro-3-(2-oxo-4-thioxo-5-thiazolidinylidene)isoindoline in 141.8 parts of dry dimethylformamide, there was added 1.3 parts of nickel (II) chloride hexahydrate. The resulting dark brown solution was stirred for one hour at room temperature under a continuous flow of nitrogen and then heated to 100° C. and maintained at that temperature for a period of approximately 4 hours during which time the solution color changed to dark green. The solution was cooled at 90° C. and filtered to remove traces of insoluble dark material. To the dark green filtrate, which was a dispersion of very finely divided particles, there was added 79.2 parts of methyl alcohol which caused agglomeration of the solid particles. The resulting solid was collected by filtration and washed with 80 parts of a mixture consisting of 50 parts of dimethylformamide and 30 parts methyl alcohol. After drying in vacuo at 80° C., there was obtained 1.7 parts of a dark-green nickel chelate pigment represented by Formula III wherein R, $R_1$ $R_2$ and $R_3$ are each chlorine.

What is claimed is:

1. A compound of the formula

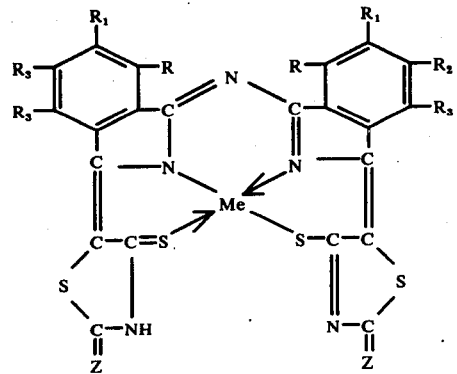

in which R, $R_1$, $R_2$ and $R_3$ are the same or different and are selected from the class consisting of hydrogen, alkyl having one to three carbon atoms, alkoxy having one to three carbon atoms, halo, trifluoromethyl, phenyl and phenyl substituted by alkyl having one to three carbon atoms, alkoxy having one to three carbon atoms or halogen; Me is a metal selected from the class consisting of copper, cobalt and nickel; and Z is oxygen or sulfur.

2. A compound according to claim 1 wherein Z is oxygen.

3. A compound according to claim 1 wherein Z is sulfur.

4. The compound according to claim 2 where in R, $R_1$, $R_2$ and $R_3$ are each hydrogen; and Me is nickel.

5. The compound according to claim 3 wherein R, $R_1$, $R_2$ and $R_3$ are each hydrogen; and Me is nickel.

6. The compound according to claim 2 wherein R, $R_1$, $R_2$ and $R_3$ are each hydrogen; and Me is copper.

7. The compound according to claim 2 wherein R, $R_1$, $R_2$ and $R_3$ are each hydrogen; and Me is cobalt.

8. The compound according to claim 2 wherein R, $R_1$, $R_2$ and $R_3$ are each chlorine; and Me is nickel.

9. The process for preparing a compound according to claim 1 which comprises interacting approximately two molecular equivalents of a compound of the formula

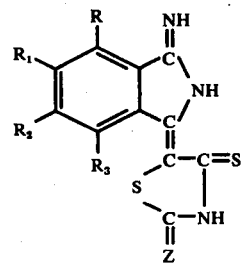

with approximately one molecular equivalent of a salt of a divalent metal, Me, wherein Me, R, $R_1$, $R_2$, and $R_3$ and Z each have the same respective meanings given in Claim 1.

* * * * *